April 7, 1936. G. A. VAN ROSSEM Plant Pat. 170
ROSE
Filed Nov. 19, 1935
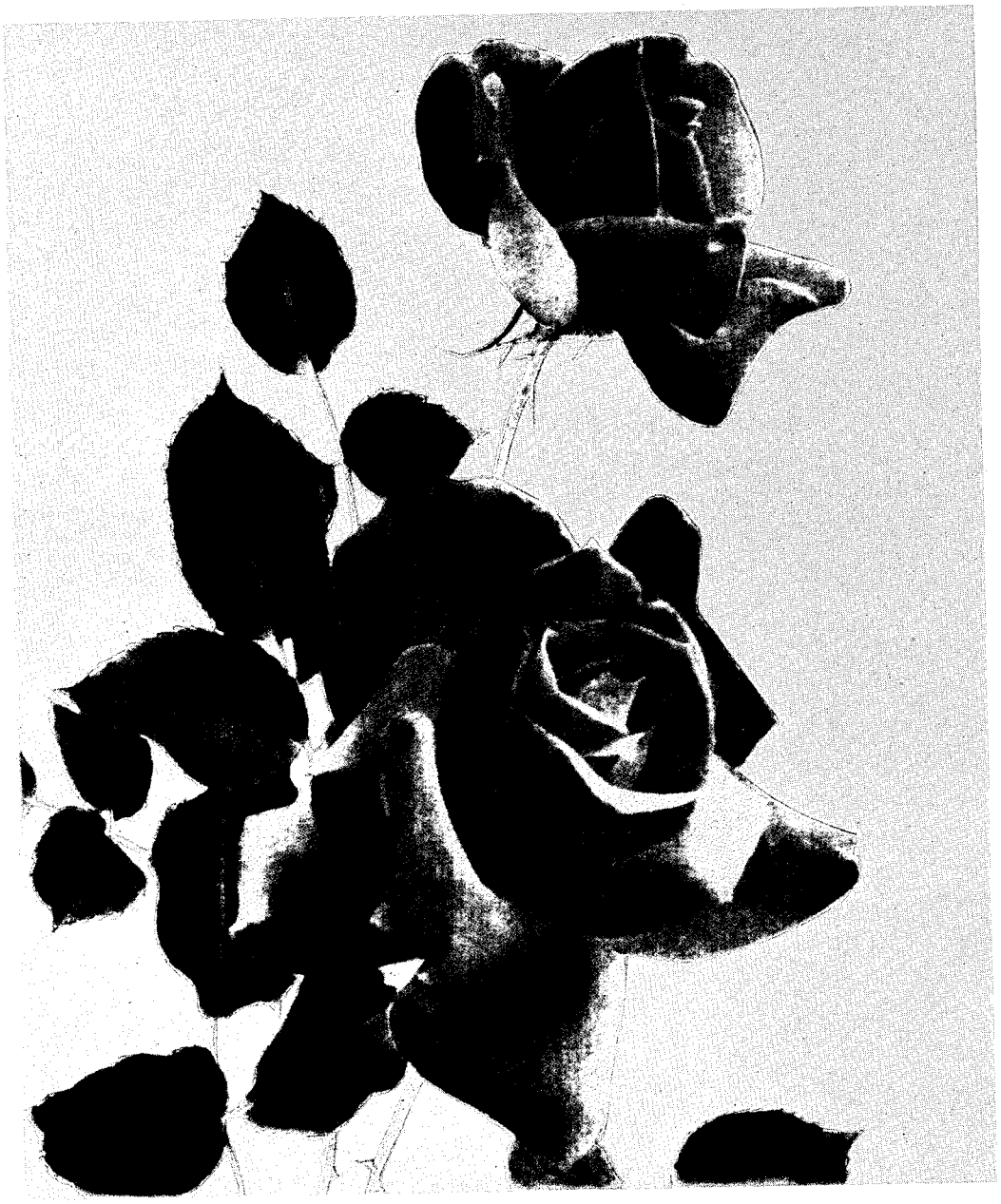
Inventor
G. A. Van Rossem
By Robert Robb
Attorney Patented Apr. 7, 1936

Plant Pat. 170

UNITED STATES PATENT OFFICE

170

ROSE

Gerard Adriaan van Rossem, Naarden, Netherlands, assignor to Jackson & Perkins Company, Newark, N. Y.

Application November 19, 1935, Serial No. 50,591

1 Claim. (Cl. 47—61)

The present discovery relates to a new and distinct variety of rose plant, having as its primary object the creation of a "double Etoile de Hollande", for which a universal desire has long existed.

While the present seedling may be considered as an improvement of the same class as this known rose, it differs therefrom in important respects, in that the bloom is slightly darker in the average run, much fuller and with the same pronounced fragrance of *R. centifolia,* generally termed "old rose perfume".

In respect to the habits of growth this new variety is much more vigorous and robust than Etoile de Hollande, and blooms more continuously without the prolonged periods of rest characteristic of Etoile de Hollande.

Everything considered, there is no other rose in commerce possessing the same general characteristics as the new variety, and as a garden rose, it meets with very great approval generally.

Asexual reproduction of this new variety shows the characteristics to be fixed.

The following is a detail description of my new rose, all reference to color being based on the Gravereaux chart:—

Parentage:
- Seedling.
- Seed parent "Chas. P. Kilham seedling".
- Pollen parent "Etoile de Hollande".

Classification:
- Botanic and commercial—Hybrid Tea.

*Flower*

Blooming habit:
- Location where observations were made, test gardens and fields at Newark, N. Y.
- Continuous.

Bud:
- *Size.*—Very large.
- *Form.*—Long, ovoid: Unaffected by wet or hot weather.
- *Color.*—When sepals first divide—maroon. When petals begin to unfurl—garnet. When half blown; inside of petals—ox blood, reverse of petals—maroon.
- *Sepals.*—Smooth edge; curl back when bud unfurls.
- *Calyx.*—Shape—funnel. Size—large. Aspect—smooth.
- *Peduncle.*—Length — long. Aspect — smooth. Color—bronzy. Strength—stiff; heavy.
- *Opening.*—Bud opens well. Unaffected by adverse conditions.

Bloom:
- *Size.*—Very large; average size when fully expanded 4″.
- *Borne.*—Singly, or several together.
- *Stems.*—Medium; strong.
- *Form.*—When first open—high center. Permanence—outer petals curl back.
- *Petalage.*—Very double (many petals and stamens hidden). Number of petals under normal conditions 40 to 50.
- *Color.*—Center of flower—garnet. Outer petals—blood red. Base of petals (aiglet)—paler. Inside of petals—blood red. Reverse of petals—garnet. General tonality from a distance—deep red.
- *Variegations.*—None.
- *Discoloration.*—General tonality at end of first day—blood red. Second day — crimson. Third day—scarlet crimson with purple cast in wet weather.

Petals:
- *Texture.*—Thick; unaffected by wet or hot weather.
- *Appearance.*—Inside velvety, outside satiny.
- *Form.*—Round.
- *Arrangement.*—Imbricated (regularly arranged shingle-like); petaloids in center—many and large.
- *Persistence.*—Drop off cleanly.
- *Fragrance.*—Strong. Nature—"Old Rose perfume" (*centifolia*).
- *Lasting quality.*—On plant and as cut flower very long.

Genital organs:
- *Stamens, anthers.*—Small, few. Color—yellow. Arrangement—regular around styles.
- *Stamens, filaments (threads).*—Medium. Color—reddish.
- *Pollen.*—Lemon yellow.
- *Styles.*—Loosely separated; short; heavy.
- *Stigmas.*—Yellow color.
- *Ovaries.*—All enclosed in calyx.

Fruit:
- Variety is fertile with its own pollen.
- *Form.*—Round.
- *Aspect.*—Smooth.
- *Color at maturity.*—Orange.
- *Sepals.*—Caducous (soon falling).

*Plant*

Form:
- Bush.

Growth:
- Vigorous.

Foliage:

Generally five leaflets.

*Size.*—Large.

*Quantity.*—Abundant.

*Color.*—New foliage—upper side—bronzy, under side—same. Old foliage—upper side—normal green, under side—lighter green.

*Shape.*—Oval pointed.

*Texture.*—Upper side leathery. Under side smooth. Ribs and veins—ordinary.

*Edge.*—Serrated (saw toothed).

*Serrations.*—Single, sharp.

*Rachis.*—Color reddish, under side smooth.

*Stipules.*—Medium length, smooth.

*Disease resistance.*—resistant.

Wood:

*New wood.*—Reddish color.

*Old wood.*—Brown color and smooth bark.

Thorns: (Divided into thorns, prickles and short needles).

*Thorns.*—Quantity—on main stalks from base, ordinary; on laterals from stalk, few. Form—broad base; medium length; straight and hooked downward. Color when young—red. Position—irregular.

*Prickles.*—Quantity—on main stalks, none; on laterals, none.

*Short Needles.*—Quantity—on main stalks, none; on laterals, none.

I claim:

A new and distinct variety of rose plant, characterized by the vigorous, robust and continuity of blooming habits of the plant, and the color, size and fragrance of its blossoms, substantially as shown and described.

GERARD ADRIAAN VAN ROSSEM.